US00PP20724P2

(12) United States Plant Patent
Jacobs

(10) Patent No.: US PP20,724 P2
(45) Date of Patent: Feb. 9, 2010

(54) ***ALSTROEMERIA* PLANT NAMED 'ZALSALAN'**

(50) Latin Name: *Alstroemeria hybrida*
Varietal Denomination: Zalsalan

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 352 days.

(21) Appl. No.: 11/820,019

(22) Filed: Jun. 15, 2007

(51) Int. Cl.
*A01H 5/00* (2006.01)

(52) U.S. Cl. ..... Plt./309

(58) Field of Classification Search ..... Plt./309
See application file for complete search history.

*Primary Examiner*—Kent L Bell
(74) *Attorney, Agent, or Firm*—C. A. Whealy

(57) ABSTRACT

A new and distinct cultivar of *Alstroemeria* plant named 'Zalsalan', characterized by its erect and strong flowering stems; vigorous growth habit; white and yellow-colored flowers with red purple-colored stripes; and excellent post-production longevity.

1 Drawing Sheet

Botanical designation: *Alstroemeria hybrida.*
Cultivar denomination: 'Zalsalan'.

BACKGROUND OF THE INVENTION

The present invention relates to a new and distinct cultivar of *Alstroemeria* plant, botanically known as *Alstroemeria hybrida*, commercially used as a cut flower *Alstroemeria,* and hereinafter referred to by the name 'Zalsalan'.

The new *Alstroemeria* is a product of a planned breeding program conducted by the Inventor in Rijsenhout, The Netherlands. The objective of the breeding program is to create new cut flower *Alstroemeria* cultivars with desirable flower and plant qualities, attractive foliage and flower coloration and excellent postproduction longevity.

The new *Alstroemeria* originated from a cross-pollination made by the Inventor in Rijsenhout, The Netherlands in May, 2001, of a proprietary *Alstroemeria hybrida* selection identified as code number 00469-4, not patented, as the female, or seed, parent with a proprietary *Alstroemeria hybrida* selection identified as code number 871069-2, not patented, as the male, or pollen, parent. The cultivar Zalsalan was discovered and selected by the Inventor as a flowering plant from within the progeny of the stated cross-pollination in a controlled environment in Rijsenhout, The Netherlands in June, 2002.

Asexual reproduction of the new *Alstroemeria* by root divisions in a controlled environment in Rijsenhout, The Netherlands since September, 2002, has shown that the unique features of this new *Alstroemeria* are stable and reproduced true to type in successive generations.

SUMMARY OF THE INVENTION

The cultivar Zalsalan has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zalsalan'. These characteristics in combination distinguish 'Zalsalan' as a new and distinct cultivar of *Alstroemeria:*

1. Erect and strong flowering stems.
2. Vigorous growth habit.

3. White and yellow-colored flowers with red purple-colored stripes.
4. Excellent postproduction longevity.

Plants of the new *Alstroemeria* can be compared to plants of the parent selections. Plants of the new *Alstroemeria* differ from plants of the parent selections primarily in flower color.

Plants of the new *Alstroemeria* can be compared to plants of the *Alstroemeria hybrida* cultivar Virginia, disclosed in U.S. Plant Pat. No. 11,331. In side-by-side comparisons conducted in Rijsenhout, The Netherlands, plants of the new *Alstroemeria* differed from plants of the cultivar Virginia primarily in flower color as plants of the cultivar Virginia did not have as pronounced yellow-colored central area on the inner lateral petal segments.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria*. The photograph comprises a side perspective view of a typical flowering stem of 'Zalsalan'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15° C. to 20° C., night temperatures ranged from 10° C. to 15° C. and light levels averaged 5,000 lux. Plants used for the photograph and description were about one year-old. The photograph and the description were taken in the spring. Color references are made to The Royal Horticultural Society Colour Chart, 1995 Edition, except where general terms of ordinary dictionary significance are used.

Botanical classification: *Alstroemeria hybrida* cultivar Zalsalan.

Parentage:

*Female, or seed, parent.*—Proprietary *Alstroemeria hybrida* selection identified as code number 00469-4, not patented.

*Male or pollen parent.*—Proprietary *Alstroemeria hybrida* selection identified as code number 871069-2, not patented.

Propagation:

*Type.*—By root divisions.

*Time to produce a rooted young plant, summer.*—About 40 days.

*Time to produce a rooted young plant, winter.*—About 60 days.

*Root description.*—Fibrous, fleshy, thick; close to 155D, in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant habit.*—Upright; freely branching, bushy appearance. Vigorous growth habit.

*Time from planting to harvest of cut flowers.*—About 80 to 90 days.

*Number of flowering stems produced per year.*—About 240 to 280.

*Plant height.*—About 120 cm to 180 cm.

*Plant diameter* (*spread*).—About 25 cm to 30 cm.

Flowering stem description:

*Aspect.*—Erect.

*Length.*—About 150 cm.

*Diameter.*—About 6 mm to 12 mm.

*Internode length.*—About 1.5 cm to 5 cm.

*Strength.*—Strong.

*Texture.*—Glabrous.

*Color.*—Close to 146C.

Foliage description:

*Appearance.*—Leaves asymmetrical; sessile.

*Length.*—About 15 cm to 20 cm.

*Width.*—About 3 cm to 4.5 cm.

*Shape.*—Lanceolate.

*Apex.*—Acute.

*Base.*—Attenuate.

*Margin.*—Entire; slightly undulate.

*Texture, upper and lower surfaces.*—Smooth, glabrous.

*Venation pattern.*—Parallel.

*Color.*—Developing and fully developed foliage, upper surface: Close to 146A; venation, similar to lamina. Developing and fully developed foliage, lower surface: Close to 146A; venation, similar to lamina.

Flower description:

*Flower type and habit.*—Single cup-shaped flowers arranged in compound umbels. Flowers face mostly outwardly. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 12 to 16 days.

*Flower buds* (*showing color*).—Length: About 3 cm to 5 cm. Diameter: About 1 cm to 2 cm. Shape: Roughly ovoid. Color: Close to 4C; towards the base, tinted with 59D.

*Umbel height.*—About 20 cm to 25 cm.

*Umbel diameter.*—About 20 cm to 25 cm.

*Number of flowers per umbel.*—About 15 to 25.

*Flower diameter.*—About 6 cm to 7.5 cm.

*Flower length* (*height*).—About 6 cm to 8 cm.

*Flower depth.*—About 6 cm to 8 cm.

*Perianth.*—Arrangement: Six arranged in two whorls, each whorl with two lateral and one median segments. Size, outer perianth: Length, lateral segments: About 6 cm to 7 cm. Width, lateral segments: About 3.5 cm to 4 cm. Length, median segment: About 6.5 cm to 8 cm. Width, median segment: About 3.5 cm to 4.5 cm. Size, inner perianth: Length, lateral segments: About 7 cm to 8 cm. Width, lateral segments: About 1.5 cm to 2.5 cm. Length, median segment: About 5.5 cm to 6.5 cm. Width, median segment: About 1.5 cm to 2 cm. Shape, outer perianth, lateral and median segments: Obovate. Shape, inner perianth, lateral and median segments: Oblanceolate. Apex, outer perianth, lateral and median segments: Embedded pointed. Apex, inner perianth, lateral and median segments: Acute. Base, outer and inner perianths, lateral and median segments: Attenuate. Margin, outer and inner perianths, lateral and median segments: Entire; weakly undulate. Texture, outer and inner perianths, lateral and median segments: Smooth, glabrous. Color, outer perianth: When opening and fully opened, lateral and median segments, upper surface: Close to 155D; apex, greenish overtones. When opening and fully opened, lateral and median segments, lower surface: Close to 155D; towards the base, tinted with 73D; apex and venation, greenish overtones. Color, inner perianth: When opening and fully opened, lateral segments, upper surface: Towards the apex and base, close to 155D; center band, close to 9A; stripes, close to 59A; apex, greenish overtones. When opening and fully opened, lateral segments, lower surface: Towards the apex and base, close to 155D; central band, close to 9A; main vein, greenish overtones. When opening and fully opened, median segments, upper surface: Close to 155D; apex, greenish overtones. When opening and fully opened, lateral segments, lower surface: Close to 155D; main vein, greenish overtones.

*Peduncles.*—Length: About 11 cm to 16 cm. Diameter: About 2 mm to 3 mm. Strength: Strong. Angle: Erect to about 20° C. from vertical. Texture: Smooth, glabrous. Color: Close to 146C; stripes, close to 185A.

*Reproductive organs.*—Stamens: Quantity per flower: Six. Filament length: About 4 cm. Filament color: Close to 65D. Anther shape: Elliptical. Anther length: About 8 mm. Anther diameter: About 3 mm. Anther color: Close to 152D. Pollen amount: Scarce. Pollen color: Close to 17C. Pistils: Quantity per flower: One. Style length: About 4 cm to 4.5 cm. Style color: Close to 65D. Stigma color: Close to 65D. Ovary color: Close to 146C. Fruit/seed: Fruit and seed development has not been observed.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from about −5° C. to about 40° C.

It is claimed:

1. A new and distinct *Alstroemeria* plant named 'Zalsalan' as illustrated and described.

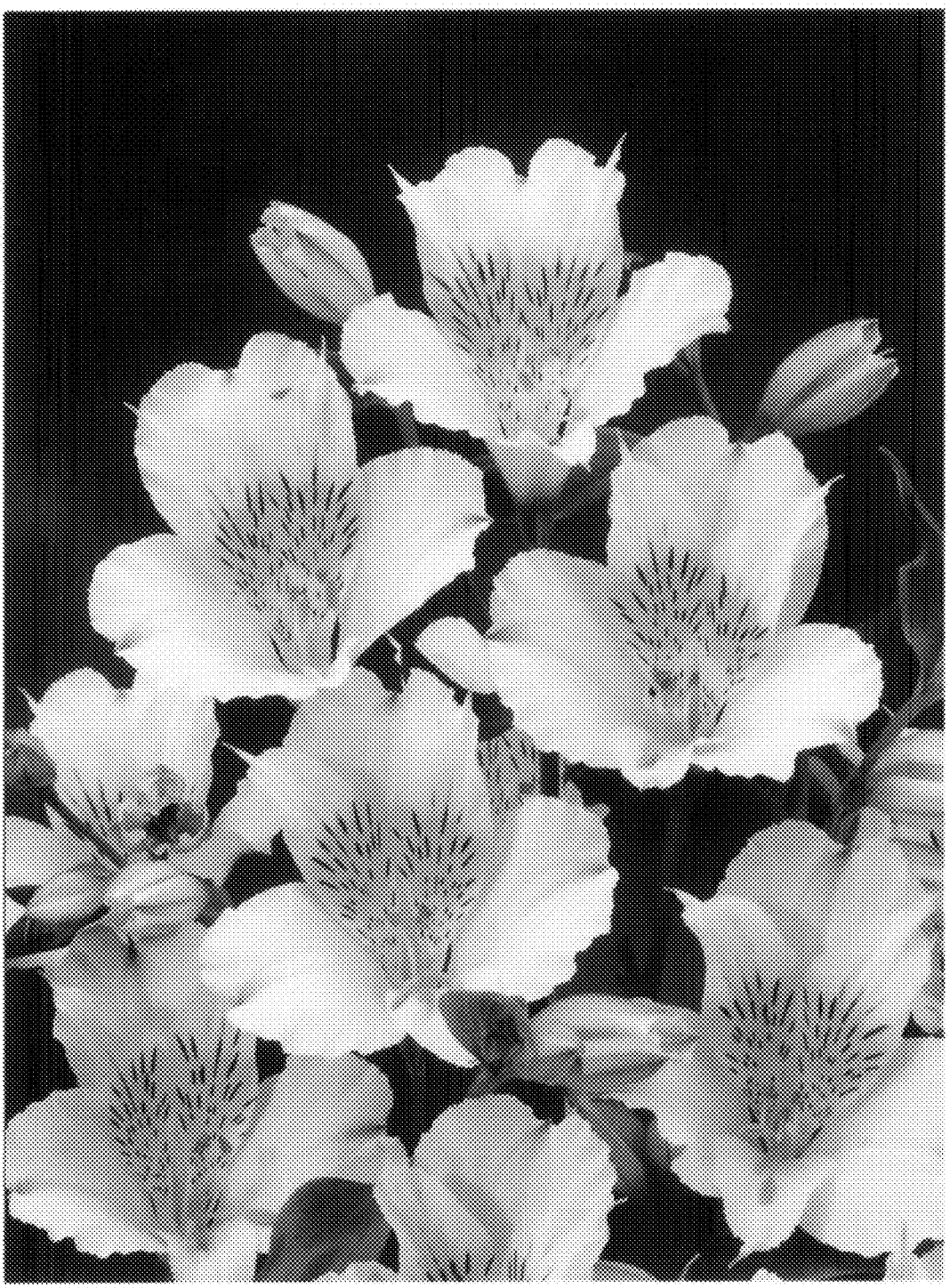

* * * * *